United States Patent [19]
Narciso, Jr.

[11] Patent Number: 5,169,395
[45] Date of Patent: Dec. 8, 1992

[54] LASER DELIVERY SYSTEM

[75] Inventor: Hugh L. Narciso, Jr., Santa Barbara, Calif.

[73] Assignee: PDT Cardiovascular, Inc., Goleta, Calif.

[21] Appl. No.: 691,696

[22] Filed: Apr. 26, 1991

[51] Int. Cl.⁵ ............................................. A61B 17/36
[52] U.S. Cl. ........................................ 606/7; 606/14; 606/15
[58] Field of Search .................... 606/2, 7, 10–16; 128/395–398

[56] References Cited

U.S. PATENT DOCUMENTS

| | | | |
|---|---|---|---|
| 4,448,188 | 5/1984 | Loeb | 606/15 X |
| 4,660,925 | 4/1987 | McCaughan, Jr. | 606/15 X |
| 4,686,979 | 8/1987 | Gruen et al. | 606/15 X |
| 4,768,858 | 9/1988 | Hussein | 606/14 X |
| 4,784,132 | 11/1988 | Fox et al. | 606/15 |
| 4,819,632 | 4/1989 | Davies | 606/15 X |
| 4,850,351 | 7/1989 | Herman et al. | 606/16 X |
| 4,860,743 | 8/1989 | Abela | 606/28 X |
| 5,071,417 | 12/1991 | Sinofsky | 606/12 X |

*Primary Examiner*—Peter A. Aschenbrenner
*Attorney, Agent, or Firm*—Michael G. Petit

[57] ABSTRACT

A system is described for the delivery of light to, and/or the receiving of light from, a target located on the wall of a tortuous tube such as a blood vessel. The delivery system is generally useful for laterally delivering and receiving light for the detection and photodynamic therapy of target tissue and is particularly useful for the treatment of atherosclerosis. When certain biocompatible photoreactive molecules such as hematoporphyrin or the like are injected into a patient the molecules are selectively taken up by target tissue such as tumors or atheromatous plaque. Subsequent illumination of the target tissue activates the photoreactive molecules causing fluorescence emission from, and destruction of, the host target tissue. The preferred embodiments comprise a hollow optical waveguide terminating in a supple diffuser tip which may be inserted over an intravascular flexible guide wire. The optical delivery catheter is advanced along the guidewire until the diffuser tip reaches the target tissue. Light of a wavelength suitable to activate previously injected photoreactive molecules is delivered to the target causing selective cell lysis and/or target tissue destruction. The disclosed system is also capable of delivering laser energy for simultaneous hyperthermic generation and photodynamic therapy.

15 Claims, 3 Drawing Sheets

LASER DELIVERY SYSTEM

BACKGROUND OF THE INVENTION

Reference to Co-pending Application

Reference is hereby made to a co-pending patent application assigned to the same assignee as the present application entitled: "Diffusion Tip for Optical Fibers," filed on Nov. 1, 1990 under Ser. No. 07/608,006.

1. Field of the Invention

This invention relates to an apparatus for delivering light to and from a target situated along the wall of a tortuous tube. More particularly, the invention relates to an improved catheter for delivering light for photodynamic therapy of atherosclerosis or for receiving an optical signal from the wall of a blood vessel which may be comprised of healthy tissue, atherosclerotic plaques, thrombus, calcium or any combination thereof.

2. Prior Art

Approximately four million people in the United States suffer from arteriosclerotic coronary artery disease. Many of these people are likely to suffer or die from myocardial infarction, commonly known as heart attack. Heart disease is, in fact, the leading cause of death in the United States. Thrombosis in the coronary artery beyond the arteriosclerotic constriction is the usual cause of heart attacks. A procedure which can open arteriosclerotic constrictions thereby permitting the normal flow of blood to the heart may reduce the many deaths and disabilities caused by heart disease.

Constrictions in the coronary artery are caused by a buildup of plaque. Plaque can occur in many forms, from a thick viscous consistency (similar to toothpaste) to a rock-hard consistency depending on the proportion of components which may include calcium, fibrous tissue, fatty deposits, organized clots and thrombus.

These deposits accumulate at one location and drastically narrow the bore of the artery thus restricting and even totally blocking the flow of blood. The site of accumulated deposits that constitute a blood vessel is referred to as stenosis while a total blockage is referred to as occlusion. Various techniques such as arterial bypass surgery, endarterectomy, balloon angioplasty and drilling procedures have been employed for removing deposits of plaque. If the plaque is of recent origin and is reasonably elastic, a balloon catheter may be used to clear the artery.

Percutaneous Transluminal Coronary Angioplasty (PTCA), described in U.S. Pat. No. 4,195,637 to Gruntzig et al issued Apr. 1, 1980 has been utilized for a number of years to treat coronary arteries narrowed by plaque deposits. A catheter having inflatable balloon secured to its distal end is advanced through an artery to a narrowed region. The balloon is then inflated with a fluid from an external source, causing the narrowed region of the artery to be expanded. The balloon is then deflated and withdrawn. A serious problem associated with balloon angioplasty has been the occurrence in up to 30% of the cases of so-called restenosis, either immediately after the procedure or within about six months. Another problem associated with PTCA is abrupt closure. This results from flaps or segments of healthy and plaque-ridden vessel wall which are formed during balloon angioplasty by the balloon catheter advancing sub-intimally and which can block the artery. Such blockage of the artery requires emergency surgery and can often result in death. Furthermore, a surgical team is required to stand by during the balloon angioplasty procedure.

To overcome the problem of abrupt closure, the flaps or segments of detached intima which are formed during the balloon angioplasty and which block the artery can be fused by heating either the wall of a special balloon in a procedure called laser balloon angioplasty (LBA) sufficiently to cause fusion of the tissue or by the passage of a hot laser tip through the expanded vessel to cause fusion.

Other techniques involving the application of heat in a coronary artery include the "hot tip" described in U.S. Pat. No. 4,646,737 issued Mar. 3, 1987 to Hussein et al and U.S. Pat. No. 4,662,368 issued May 5, 1987 to Hussein et al wherein a thermally conductive tip located at the end of a catheter is heated by laser radiation and conducts heat to the surrounding region as it is pushed through a narrowed artery. The hot tip reaches temperatures on the order of several hundred degrees Celsius in order to produce the necessary conductive heating as it is pushed through the artery. The hot tip is unable to expand the artery beyond the conductive tip diameter, which must be limited by the introduction site lumen and by the caliber of the artery being treated. Moreover, most total stenoses or occlusions and totally calcified blockages cannot be treated by balloon angioplasty. Even a "hot tip" catheter cannot open up a totally calcified blockage.

Prior art techniques have been disclosed for directing laser radiation outwardly from the tip of an optical fiber to vaporize plaque. An optical fiber surrounded with a scattering medium for producing a cylindrical pattern of light at the tip of an optical fiber is disclosed in U.S. Pat. No. 4,660,925 issued Apr. 28, 1987 to McCaughan, Jr. and in copending U.S. patent application Ser. No. 07/608,006. None of the prior art techniques taken alone provide the combination of small diameter, flexibility, power handling capability and compatibility with a guide wire necessary for the permanent removal of plaque from a blood vessel.

Spears, in U.S. Pat. No. 4,773,899 issued Sep. 27, 1988, incorporated herein by reference, teaches the administration of a hematoporphyrin, preferably by intravenous injection to an atherosclerotic patient to be treated. The hematoporphyrin when administered intravenously, is selectively absorbed into the atheromatous plaque, with little or no absorption into healthy areas of the arterial wall. Upon illumination of the atheromatous plaque containing the exogenous chromophore, the hematoporphyrin is activated. The activated hematoporphyrin facilitates the destruction and sloughing off of the host atheromatous plaque tissue.

Illumination of the plaque has been achieved by different techniques. With one technique, the method for which the present invention is particularly well suited, the patient is catheterized with a light-emitting catheter inserted into the diseased vessel so that the light-emitting portion of the catheter is adjacent to the atheromatous plaque. Alternatively, a form of liquid light such as firefly luciferin-luciferase is injected into the vasculature such that the liquid light, which mixes freely with blood or blood replacement, perfuses the diseased artery.

Spears, in U.S. Pat. No. 4,512,762, teaches the use of a special light-emitting balloon catheter for photoatherolytic therapy (PAT). The balloon catheter includes (a) an inflatable balloon secured to one end of the catheter tube for inflation with a gas or liquid from a remote source, and (b) at least one optical fiber which extends through the catheter lumen for transmission of light from an external light source to the interior of the balloon, and (c) a light-scattering device within the balloon in the form of a hollow, liquid-filled tube. The liquid filling the tube is selected for optimal transmission of light and maximum light scattering.

Use of Spears balloon catheter provides for a more or less transparent optical path between the diffuser and the plaque by displacement of the blood (which is opaque to light at short visible wavelengths) between the external balloon surface and the arteriosclerotic plaque by inflation of the balloon. In operation, Spears' catheter stems the flow of blood along a vessel and requires intermittent and cyclical illumination-inflation/deflation of the balloon so as to minimize interruption of blood flow to the vital organs and to avoid potential problems due to heating of the balloon material and the blood of the patient undergoing treatment. In view of the growing use of PAT and the shortcoming of the prior art devices, it is desirable to provide a light delivery system which: (a) can be advanced over a guidewire; and (b) is sufficiently supple to be able to follow a tortuous path; (c) does not require inflation of a balloon to interrupt blood flow during illumination; and (d) can receive light emitted by a target tissue for fluorescence detection.

SUMMARY OF THE INVENTION

It is an object of the present invention to provide an improved light delivery system for treatment of arteriosclerosis by photoatherolytic therapy.

It is a further object of the present invention to provide a guide wire-compatible catheter for the lateral transmission of light to activate photosensitized artheromatous plaque located upon the wall of a blood vessel.

It is yet a further object of the present invention to provide a delivery system which can laterally illuminate artheromatous plaques without interruption of blood flow to the vital organs.

It is another object of the present invention to provide an apparatus for delivering light to a target which can be used in tortuous and/or tightly constricted blood vessels.

It is yet another object of the present invention to provide a laser delivery system which can be advanced along a guide wire and easily maneuvered along an artery or other blood vessel.

It is yet another object of this invention to provide a device useful for locating target tissue upon the wall of a tube the largest tissue having high specific affinity for an exogenous photosensitizing agent, comprising the steps of: (a) injecting a target tissue-specific fluorescing photosensitizing agent into a patient; (b) lateral irradiation of the target tissue; and (c) detection of the characteristic fluorescence emission by the host target tissue.

It is another object of this invention to provide a guidewire-compatible intravascular catheter useful for delivering light energy to a target tissue along the wall of a blood vessel and for receiving fluorescence light from endogenous chromophores within a target tissue and conducting the fluorescence light to a fluorescence detector.

It is still another object of this invention to provide a guidewire-compatible catheter useful for simultaneous photoatherolytic therapy and hyperthermia.

Other objects and further scope and applicability of the present invention will become apparent from the detailed description to follow taken in conjunction with the accompanying drawings.

DESCRIPTION OF THE PREFERRED EMBODIMENTS

Figure 1:
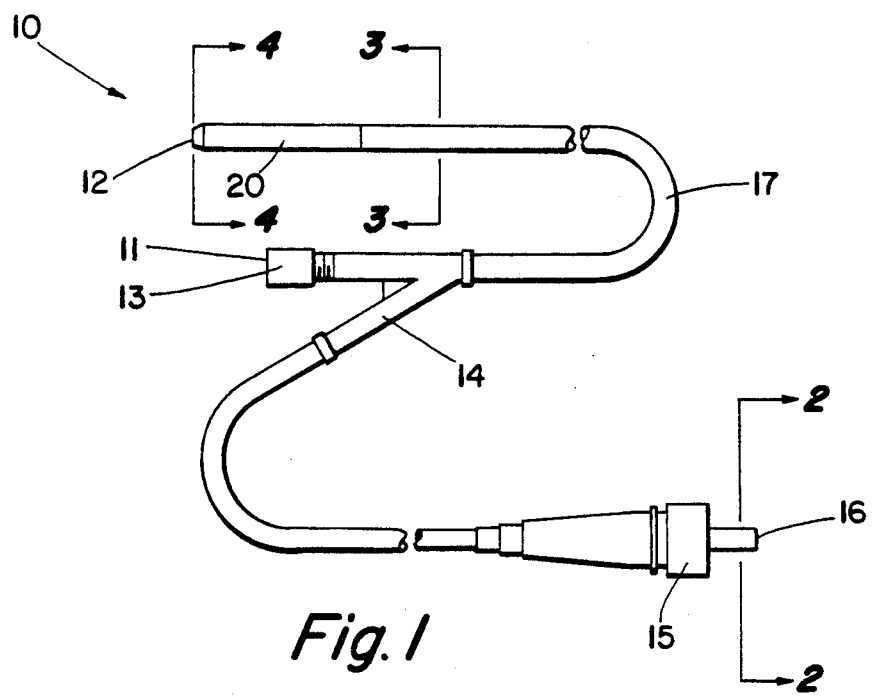
FIG. 1 is a schematic diagram of the light delivery catheter of the present invention.

While laser delivery systems have been developed to treat cardiovascular disease using PAT, four problems remain: (1) guidance of the laser delivery system to the desired treatment site when the site is along a tortuous or constricted path; (2) the catheter should be able to detect the presence of target tissue as well as deliver PAT light (3) long-term treatment of the underlying arteriosclerotic tissue not removed during the procedure (palliation vs. elimination of virtually all the diseased tissue); (4) smooth muscle cell proliferation subsequent to angioplasty and (5) the need to interrupt the flow of blood during PAT illumination necessarily requires intermittent inflation and deflation of a balloon to minimize damage to tissue downstream from the area to be treated. The present invention overcomes all of the above-mentioned problems, some or all of which are encountered with prior art devices.

First, it is necessary to introduce or guide the light delivery system to the target tissue. In the case of PAT, prior art methods of guiding laser angioplasty delivery systems include:

a) standard PTCA guide wires (assuming that the light delivery system is flexible enough to follow the guide wire, this guiding system limits the use of the delivery system to subtotal occlusions);

b) PTCA balloon dilatation aiming (ineffective in tortuous arteries);

c) guidance under a fluoroscope (not 3-dimensional) gives topographic information on areas which receive blood flow, but no information on the disease;

d) angioscopy;

e) extravascular ultrasound-color flow Doppler (not 3-dimensional);

f) intravascular ultrasound (presently cannot view in the forward direction, but only gives information perpendicular to the ultrasound catheter tip); and g) Spectroscopic fluorescence guidance (fluorescent emissions of atheroma and healthy tissue are too similar to truly differentiate consistently): that is; the diseased tissue is inexorably intertwined in the host healthy tissue.

The novel light delivery system described herein is a highly flexible light-conducting catheter designed to be used over a guidewire for safety. The guidewire is intended to lead the catheter through tortuous and constricted pathways such as arteries. For this reason, flexibility of the catheter is important. The catheter must be flexible enough to track the guidewire along a serpentine route. A stiff catheter would tend to lead the guidewire with resulting perforation of the arterial wall. A dedicated guidewire lumen is, therefore, incorporated into this delivery system to house the guidewire. This allows the guidewire to remain in place during positioning and treatment. The treatment, or light conducting fibers never come in contact with the guidewire.

The catheter of the present invention is also adaptable for use with a fluorescence probe. A fluorescence probe may be used to detect either endogenous fluorescent molecules in target tissue or elevated levels of exogenous chromophores such as hematoporphyrin derivative (HpD), dihematoporphyrin ether (DHE), or tin etiopurpurin ($SnET_2$). For exogenous chromophores such as HpD the excitation wavelengths employed is 630 nanometers.

Turning now to FIG. 1 a guide wire-compatible light delivery catheter useful for PAT is generally indicated at 10. The catheter has a proximal end 11, a distal end 12 and an optical connector end 16. Illuminating light enters the catheter 10 through the fiber optic bundle housed within a SMA connector 15 located at the optical connector end 16 of the catheter. The fiber optic bundle constitutes a portion of an optical waveguide which provides optical communication between the optical connector end 16 of the catheter and the distal or treatment end 12 of the catheter.

Figure 2:
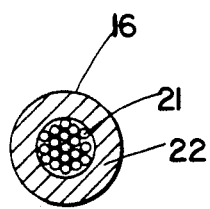
FIG. 2 is a cross-section of the light delivery catheter of FIG. 1 along line 2—2.

The optical connector end 16 of the catheter is shown in cross section in FIG. 2 and comprises a fiber optic bundle 21 enclosed within a stainless steel connector 22. The illuminating light travels along the fiber optic bundle portion of the optical waveguide until it passes through the Y adaptor 14 into the catheter body 17 where the fibers comprising the bundle are separated to surround a guidewire lumen. The guidewire lumen is a hollow conduit of a diameter sufficient to accommodate a guidewire therewithin extending between the distal end 12 of the catheter and the guidewire port 13. The guidewire lumen is indicated at 31 in the catheter cross-section shown in FIG. 3 and end view of the catheter tip in FIG. 4.

Figure 3:
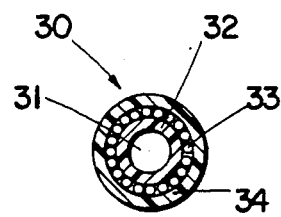
FIG. 3 is a cross-sectional view of the light delivery catheter of FIG. 1 along line 3—3.
Figure 4:
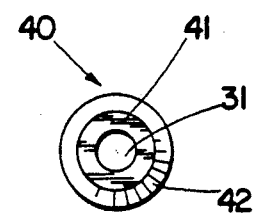
FIG. 4 is an end view of the light delivery catheter of FIG. 1 along line 4—4.

As mentioned previously, after it passes the Y adapter 14, the fiber bundle is opened to surround and track the guidewire lumen as the optical waveguide continues along the body 17 of the catheter. The spacial relationship between the fiber bundle and the guidewire lumen within the main body of the catheter is shown in FIG. 3. The guidewire lumen 31 is surrounded by an inner tubing 32 through which the guidewire may pass. The inner tubing 32 is, in turn, surrounded by the (now divided) optical fiber array. The entire catheter body 17 is finally enclosed in a durable jacket or outer tubing 34.

Figure 5:
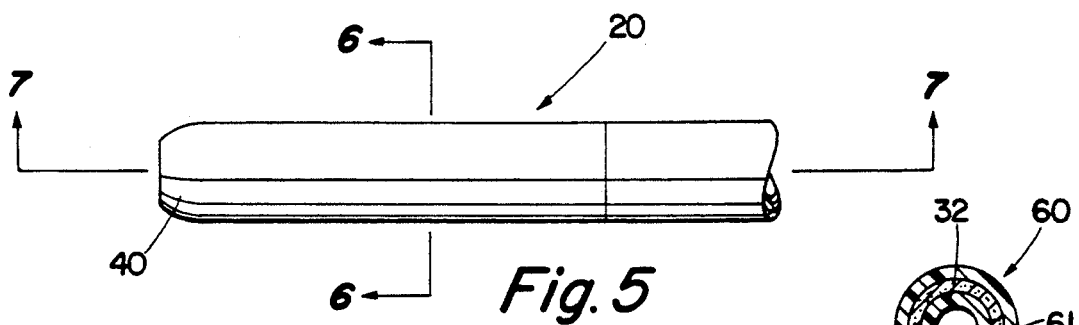
FIG. 5 is a plan view of the distal tip of the light delivery catheter of FIG. 1.

As the illuminating light continues along the optical waveguide through the catheter body 17 it reaches the diffuser tip 20. The diffuser tip generally indicated at 20 in FIG. 5 comprises a cylindrical diffuser portion 51 and a cap portion 40. The cap is enclosed with a radiopaque and light-opaque outer rounded plastic covering which facilitates passage of the catheter through a vessel and facilitates fluoroscopic placement of the tip.

Figure 6:
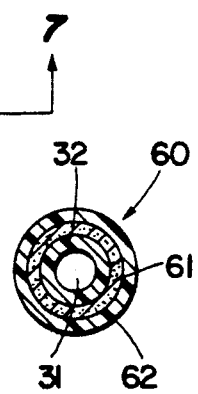
FIG. 6 is a cross-section of the distal tip of the light delivery catheter of FIG. 5 taken along line 6—6.
Figure 7:
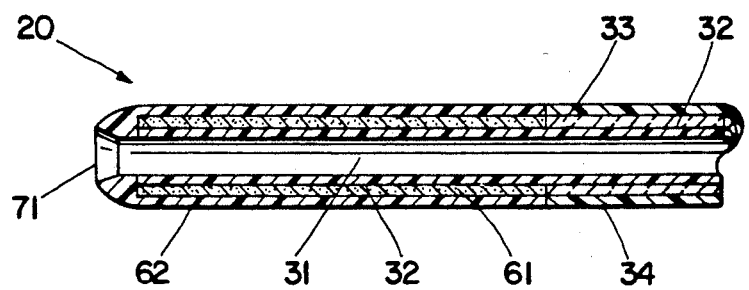
FIG. 7 is a longitudinal cross-section of the distal tip of the light delivery catheter of FIG. 5 taken along line 7—7.

The construction of the diffuser tip 20 is shown in cross section in FIG. 6 and longitudinal cross section in FIG. 7. The cylindrical diffuser 20 comprises a central guide wire lumen 31 surrounded by an inner tubing 32. The inner tubing is enveloped in a layer of a diffusing material 61 such as doped silicone which diffuser material 61 is, in turn, enclosed within an outer jacket of optically clear plastic tubing 62. The distal end 71 of the cylindrical diffuser comprises the cap which is shown in cross section in FIG. 4.

Light conducted along the optical fiber array 33 enters the transparent diffusing material 61 where it is scattered laterally by embedded scattering centers thereafter to exit the cylindrical diffuser through the transparent jacket 62 and enter the surrounding target tissue.

Conversely, light emitted by surrounding target tissue may enter the cylindrical diffuser tip through the transparent jacket 62 whence it will encounter scattering centers and be deflected into the fiber optic array 33 of the catheter body 17 where it will be conducted to the optical connector end 16 and detected. Thus, a single catheter may be used to both detect and treat atheromatous plaque.

Figure 8:
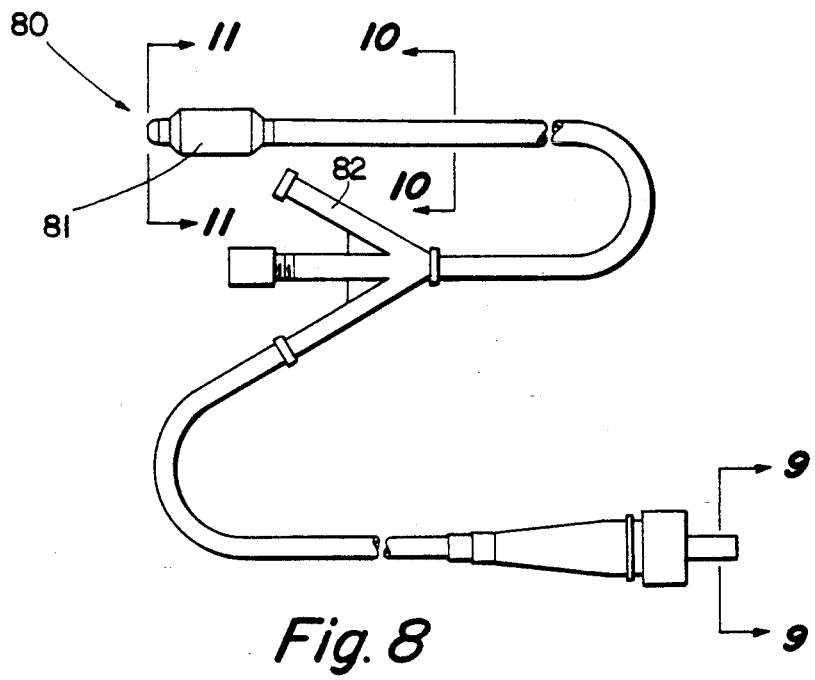
FIG. 8 is a schematic diagram of a second preferred embodiment of a light delivery catheter of the present invention employing a balloon.
Figure 9:
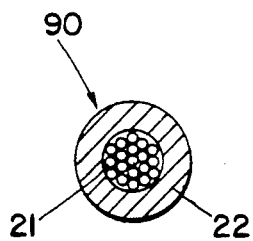
FIG. 9 is a cross-sectional view of the proximal (connector) end of the second preferred embodiment of FIG. 8 taken along line 9—9.
Figure 10:
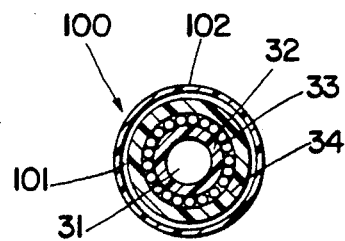
FIG. 10 is a cross-sectional view of the second preferred embodiment of the light delivery system of FIG. 8 taken along line 10—10.
Figure 11:
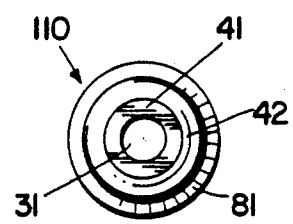
FIG. 11 is a cross-sectional view of the second preferred embodiment of the light delivery system of FIG. 8 taken along line 11—11.

There are times when it would be desirable to have a balloon available for angioplasty on the same PAT catheter or for the occlusion of the vessel if desired. A second preferred embodiment of a light delivery catheter employing a balloon at its distal end is indicated at 80 in FIG. 8. The catheter 80 is identical to the catheter shown in FIG. 1 except that an inflatable balloon 81 surrounds at least a portion of the cylindrical diffuser tip. The catheter includes a balloon inflation port 82 and an inflation channel providing fluid communication between the inflation port 82 and the interior of the balloon 81. The optical input port 90, shown in cross-section in FIG. 9, is identical to the optical input port of the first preferred embodiment shown in FIG. 2. The cross-section of the catheter body 100 shown in FIG. 10 has, in addition to the fiber optic array 33 a balloon inflation channel 101 created by an outer tube 102 providing fluid communication between the inflation port 82 and the interior of the balloon 81. An end view of the cap to the cylindrical diffuser is shown in FIG. 11 and may include, in addition to the element of the diffuser cap shown in FIG. 4, a balloon 81 surrounding the diffuser tip cap in fluid communication with the inflation port 82 by means of the inflation conduit 101.

Figure 12:
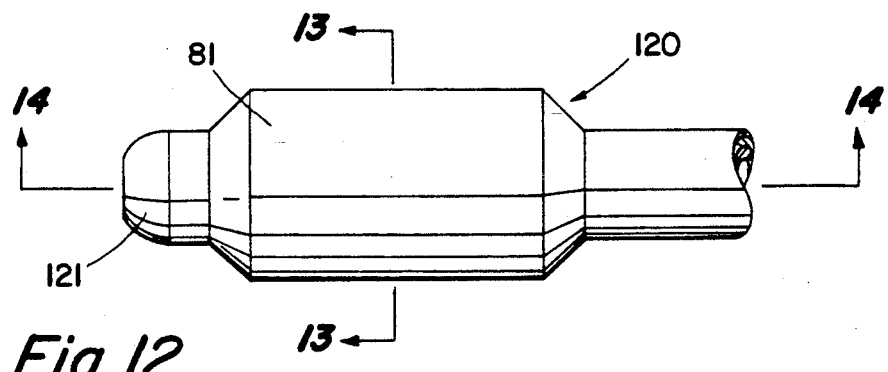
FIG. 12 is an enlarged plan view of the distal diffuser tip and balloon of the second preferred embodiment of the light delivery catheter of FIG. 8.
Figure 13:
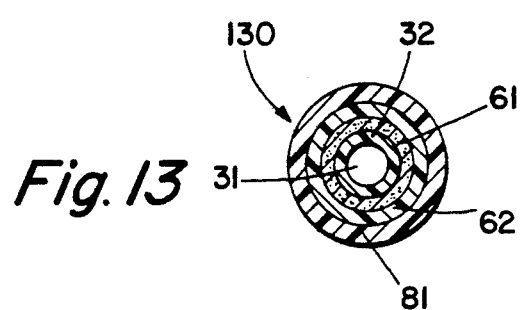
FIG. 13 is a cross-sectional view of the balloon-diffuser tip of FIG. 12 taken along line 13—13.
Figure 14:
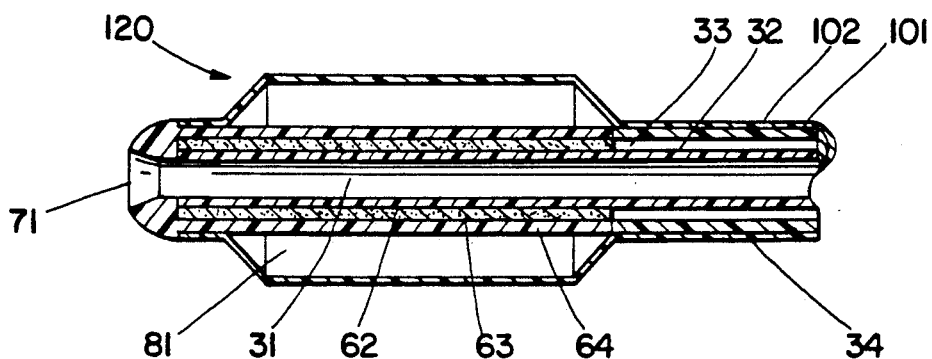
FIG. 14 is a longitudinal cross-sectional view of the distal tip of the catheter of FIG. 12 along line 14—14.

The balloon, generally indicated at 120 in FIG. 12 comprises an expandable elastomeric envelope 81 surrounding the cylindrical diffuser tip. The construction of the balloon diffuser tip is shown in detail in FIGS. 13 and 14. FIG. 13 shows a cross-sectional view of the balloon diffuser tip along line 13—13. The cross-section view is identical to that of FIG. 6 except an inflatable balloon 81 surrounds the outer transparent jacket of the diffuser tip. The balloon is inflatable by means of injection through the inflation port (not shown in FIG. 14) and inflation channel 101.

Figure 15:
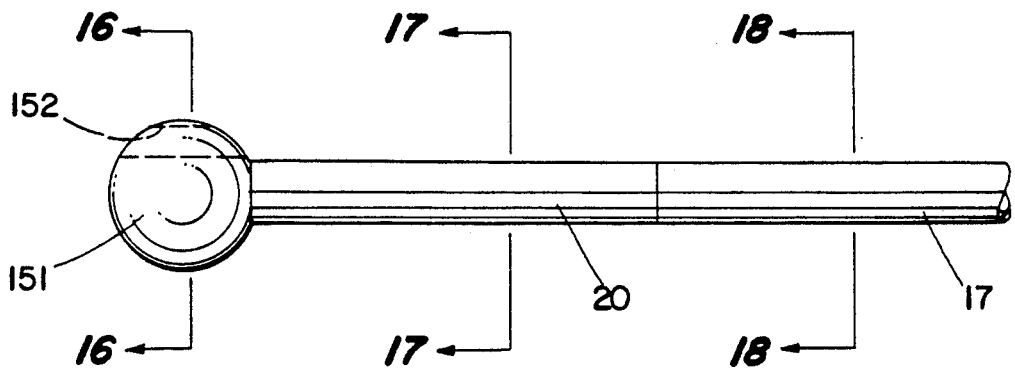
FIG. 15 shows the distal tip of a third preferred embodiment of a guidewire-compatible light delivery system having an eccentric guidewire lumen.

A third preferred embodiment of the light delivery catheter employing an abbreviated guide wire lumen is shown in FIG. 15. This embodiment obviates the need for a hollow catheter thereby providing more room for the accommodation of an optical waveguide.

Figure 16:
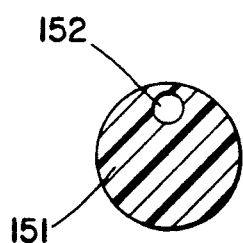
FIG. 16 is a cross-sectional view of the distal catheter tip of FIG. 15 taken along line 16—16.
Figure 17:
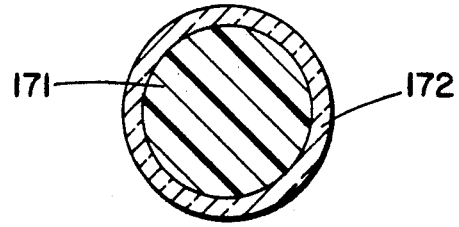
FIG. 17 is a cross-sectional view of the distal catheter tip of FIG. 15 taken along line 17—17.
Figure 18:
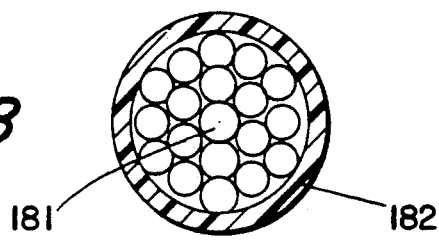
FIG. 18 is a cross-sectional view of the distal catheter tip of FIG. 15 taken along line 18—18.

In the embodiment, the main catheter body 17 terminates in a cylindrical diffuser tip as previously discussed. The cross-sectional view (FIG. 18) of the catheter body 17 is different from those of the previous two embodiments in that the fiber optic bundle 18 surrounded by an opaque plastic jacket extends, undivided, all the way to the diffuser tip. A single fiberoptic can be used in place of the bundle where flexibility is not as critical (i.e. the peripheral vasculature). The cylindrical diffuser tip, shown in cross section in FIG. 17, comprises a silicone core 171 containing scatterers surrounded by transparent plastic tubing 172. The cylindrical diffuser tip is terminated in a radiopaque plastic cap 151 with a short guide wire lumen 152 passing therethrough. The cap, which is rounded to facilitate entry, is shown in cross section in FIG. 16.

Each of the above embodiments may optionally be fitted with an additional pickup fiber external to the cylindrical diffuser tip which can transmit a portion of the light energy emanating from the diffuser and conduct it to a detector. The addition of such a pickup fiber, which must be of small diameter to avoid casting a shadow on the vessel wall, is particularly useful for monitoring the energy delivered from the diffuser tip to the surrounding tissue.

The foregoing embodiments do not require the interruption of blood flow in order to be useful for PAT. If light in the wavelength range of 630-1100 nanometers is used for illumination, the intervening blood between the cylindrical diffuser tip and the wall of the vessel will not absorb appreciable light.

What I claim is:

1. A guidewire-compatible intraluminal catheter for delivering light energy from a source of optical energy to, or receiving an optical signal from, a tissue undergoing optical energy treatment, said light energy being delivered in a uniform cylindrical pattern, said catheter comprising:
   (a) a tubular body portion having a proximal end and a distal end and a guidewire lumen;
   (b) a cylindrical optically transmissive member extending along at least a portion of the length of said body portion, said cylindrical optically transmissive member terminating at said distal end of said body portion;
   (c) a flexible tubular cylindrical diffuser tip having a proximal end attached to the distal end of said body portion in optical communication with said optically transmissive member, and distal end, said distal end having an opaque cap attached thereto;
   (d) an optical input port for coupling energy from said source of optical energy into said optically transmissive member.

2. The guidewire-compatible intraluminal catheter of claim 1, wherein said optically transmissive member comprised a cylindrical array of optical fibers.

3. The guidewire-compatible intraluminal catheter of claim 2 wherein said optical fibers further comprise a cylindrical diffuser tip.

4. The guidewire-compatible intraluminal catheter of claim 1 wherein said optically transmissive member comprises a tubular elastomeric optical waveguide of integral construction.

5. The guidewire-compatible intraluminal catheter of claim 4 wherein light scattering centers are embedded in at least a portion of said tubular elastomeric optical waveguide.

6. The guidewire-compatible intraluminal catheter of claim 1 wherein said source of optical energy is a laser.

7. The guidewire-compatible intraluminal catheter according to claim 1 wherein said cap attached to the distal end of said cylindrical diffuser tip comprises a substantially tapered radiopaque terminus for said cylindrical diffuser tip, said cap having a substantially conical hole passing therethrough for guiding said guidewire into the central lumen of the cylindrical diffuser tip.

8. The guidewire-compatible intraluminal catheter of claim 1 wherein said guidewire lumen is coaxial with said tubular body portion.

9. The guidewire-compatible intraluminal catheter of claim 8 wherein said cylindrical diffuser tip has a guidewire lumen passing through the center thereof, said guidewire lumen in said cylindrical diffuser tip connecting said proximal and distal ends of said cylindrical diffuser tip.

10. The guidewire-compatible intraluminal catheter of claim 1 wherein said guidewire lumen is attached to said body portion and parallel to, but not coaxial with, said tubular body portion.

11. A guidewire-compatible intravascular catheter for either delivering optical energy to, or receiving optical energy from, a tissue located along the wall of a blood vessel, said catheter comprising:
   (a) an elongate tubular body portion having an optically transmissive member passing therethrough and having a proximal end and a distal end;
   (b) a flexible cylindrical diffuser tip comprising optically transparent silicone with scattering centers embedded therein, said diffuser tip having a proximal end attached to said distal end of said body portion, and a distal end, said distal end of the cylindrical diffuser tip having a cap attached thereto;
   (c) an optical input port for coupling energy from said source of optical energy into said optically transmissive member of the conduction of fluorescence energy from said tissue to a fluorescence energy detector;
   (d) an inflatable balloon comprising an optically transmissive inflatable elastomeric bag symmetrically enclosing and enveloping said cylindrical diffuser over at least a portion of the length thereof; and
   (e) means for inflating and deflating said balloon.

12. The improved guidewire-compatible intravascular catheter according to claim 11 wherein said optically transmissive material comprise a tubular optical fiber bundle.

13. The improved guidewire-compatible intravascular catheter according to claim 11 wherein said optically transmissive material comprises an elongate tubular silicone core.

14. The improved guidewire-compatible intravascular catheter of claim 11 wherein said source of optical energy is a laser.

15. The guidewire-compatible intravascular catheter according to claim 11 wherein said cap attached to the distal end of said cylindrical diffuser comprises a substantially tapered radiopaque terminus for said cylindrical diffuser tip, said cap having a peripherally located, substantially cylindrical hole passing therethrough for accepting said guidewire.

* * * * *